US00PP10396P

United States Patent [19]

Trees

[11] Patent Number: Plant 10,396

[45] Date of Patent: May 12, 1998

[54] GERANIUM PLANT NAMED 'PINK PASSION'

[75] Inventor: Scott C. Trees, Arroyo Grande, Calif.

[73] Assignee: Ball Horticultural Company, West Chicago, Ill.

[21] Appl. No.: 697,259

[22] Filed: Aug. 21, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 9,921 6/1997 Dümmen ..... Plt./87.12

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

The new and distinct *Pelargonium* × *hortorum* × *Pelargonium peltatum* cultivar named 'Pink Passion' is provided. This new ivy/Zonal Geranium was the result of a controlled breeding program wherein a plant designated 6733-16 (non-patented in the United States) was pollinated by a plant designated 7012B-9 (non-patented in the United States). The new cultivar forms attractive small single deep pink florets having a dark rose eye on each petal. The small medium green foliage is well retained during shipment. The growth habit is compact and self-branching and does not require the use of a growth regulator.

1 Drawing Sheet

SUMMARY OF THE INVENTION

The present invention comprises a new and distinct Geranium cultivar, botanically known as *Pelargonium* × *hortorum* × *Pelargonium peltatum*, and hereinafter is referred to by the cultivar name 'Pink Passion'.

The new cultivar is a product of a planned breeding program which had the objective of the creation of a new Geranium cultivar that exhibits uniform round umbels, medium green foliage, a compact growth habit, and excellent basal-branching in the absence of a growth regulator.

The breeding program that resulted in the production of the new cultivar of the present invention was carried out in a controlled environment during 1993 at Arroyo Grande, Calif. U.S.A. The female parent (i.e., seed parent) was a plant designated 6733-16 (non-patented in the United States) which exhibits single hot pink florets with an eye and medium green foliage. The male parent (i.e., pollen parent) was a plant designated 7012B-9 (non-patented in the United States) which exhibits semi-double light pink florets with medium green foliage. The parentage of the new 'Pink Passion' cultivar can be summarized as follows:

6733-16 × 7012B-9.

'Pink Passion' was discovered and selected during 1993 as a highly distinctive flowering plant from among the progeny of the stated cross at Arroyo Grande, California, U.S.A. This plant was initially designated BFP-1313.

It was found that the new cultivar of the present invention:

(a) exhibits attractive small single deep pink florets having a deep rose eye on each petal,
(b) forms attractive small medium green foliage with slight zonation, and
(c) exhibits a compact cascading self-branching growth habit in the absence of a growth regulator.

After senescence the flowers abscise and drop. To date, observations of the new 'Pink Passion' cultivar have not demonstrated resistance to Botrytis or any other specific disease.

The first act of asexual reproduction of the 'Pink Passion' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1994 has demonstrated that the combination of unique characteristics as herein described for the 'Pink Passion' cultivar is fixed and is retained through successive generations of such asexual reproduction.

The new 'Pink Passion' cultivar has not been observed under all possible environmental conditions. Accordingly, the described phenotype may vary somewhat with variations in the environment, such as temperature, light intensity, and day length.

The new cultivar of the present invention provides a unique ivy/Zonal Geranium cross that displays a distinctive multiflora appearance. The uniqueness of the new cultivar readily has been confirmed through the combined presence of small dark pink flowers with a dark rose eye, small dark green foliage, and the compact and cascading growth habit of the overall plant.

The new cultivar of the present invention is being marketed under the Galleria trademark.

BRIEF DESCRIPTION OF THE PHOTOGRAPH

The accompanying photograph shows the new 'Pink Passion' cultivar with colors being as nearly true as it is reasonably possible to make the same in a color illustration of this character. The plant was being grown in a greenhouse at West Chicago, Ill., U.S.A. The general appearance of the overall plant including the flower and foliage characteristics is illustrated.

DETAILED DESCRIPTION

The following observations, measurements and comparisons describe plants grown in greenhouses located at West Chicago, Ill., U.S.A., under conditions which approximate those generally used in commercial practice. In the following description, color references are made to The R.H.S. Colour Chart of The Royal Horticultural Society, London.

England. The color values were determined on September 22nd, under natural light conditions of 200 footcandles.

Classification:

*Botanical.—Pelargonium × hortorum × Pelargonium peltatum*, cv. 'Pink Passion'.

*Commercial.*—Ivy/Zonal Geranium.

Inflorescence

A. Umbel:

*Average diameter.—Approximately* 5.5 to 7 cm.

*Average depth.—Approximately* 4.5 to 5 cm.

*Peduncle length.—Approximately* 6.3 to 11.4 cm.

*Pedicel length.*—Approximately 1.5 to 1.8 cm.

*Number of umbels plant.—When grown in a* 10 cm. pot at 9 weeks after the sticking of a rooted cutting, there commonly are approximately 2 to 4 umbels per plant.

*Number of florets/umbel.*—When grown in 10 cm. pots at 9 weeks, approximately 10 to 14 florets per umbel commonly are formed.

*Buds.*—Elliptic and lateral facing in configuration, initially Red-Purple Group 62D and changing to Red Group 52C at the time of opening, and approximately 6 to 8 mm. in length and approximately 4 to 5 mm. in width.

*Pedicels.*—Commonly approximately 1.5 to 1.8 cm in length.

B. Corolla:

*Average diameter.—Approximately* 4.2 to 4.3 cm.

*Form.*—Single and occasionally with one petaloid.

*Petals.*—Spatulate shaped, irridescent in appearance, and smooth. Commonly five non-imbricate petals are present per floret.

*Number of petaloids.—When present, commonly only a single petaloid is observed.*

*Color.*—General tonality from a distance of three meters: Bright pink. Adaxial: Red-Purple Group 66B with the lower three petals having a spot of Red Group 53C near the base and the upper two petals having larger areas of Red Group 53C commonly overlapped with a small area of Red-Purple Group 66D to Red-Purple Group 62D at the base. The petal coloration tends to fade somewhat with age. Abaxial: Red-Purple Group 66C with veins of Red-Purple Group 66B.

C. Reproductive organs:

*Androecium.—The anthers are commonly approximately* 2 to 2.5 mm. in length. The pollen color is Orange Group 28A. The filaments are approximately 6 to 7 mm. in length.

*Gynoecium.—The pistil length commonly is approximately* 12 mm. There is a single stigma which commonly has a length of approximately 7 mm. which branches into 5 parts, the ovary is approximately 2 mm. in length and the style length is approximately 3 mm.

*Fertility.*—Commonly does not produce fruits in the absence of mechanical fertilization.

D. Spring flowering response period: Approximately 6 to 7 weeks from rooted cuttings under standard greenhouse conditions.

E. Outdoor flower production: Freely flowering under outdoor growing conditions with substantially continuous blooming.

F. Durability: Ships well.

Plant

A. Foliage: Medium green with slight zonation. The leaf texture is pilose, and the rib and vein pattern is palmate.

*Form.—Reniform, with a cordate base.*

*Margin.—Bi-crenate.*

*Color.*—Adaxial: Yellow-Green Group 147B with a ring around the center of Yellow-Green Group 147A. Abaxial: Yellow-Green Group 147B.

*Size.*—Approximately 5 to 7 cm. in width at the widest point and approximately 4.5 to 6.5 cm. in length.

*Petioles.*—Are pubescent and approximately 2.6 to 2.8 cm. in length.

B. General appearance and form:

*Branching pattern.*—Freely basal-branching. No pinching is required to obtain self-branching. A compact cascading self-branching growth habit is observed in the absence of a growth regulator.

*Height.*—Approximately 14 to 20 cm. above a 10 cm. pot at 9 weeks under standard greenhouse conditions.

I claim:

1. A new and distinct cultivar of Geranium plant named 'Pink Passion', substantially as herein shown and described, which:

(a) exhibits attractive small single deep pink florets having a deep rose eye on each petal, (b) forms attractive small medium green foliage with slight zonation, and (c) exhibits a compact cascading self-branching growth habit in the absence of a growth regulator.

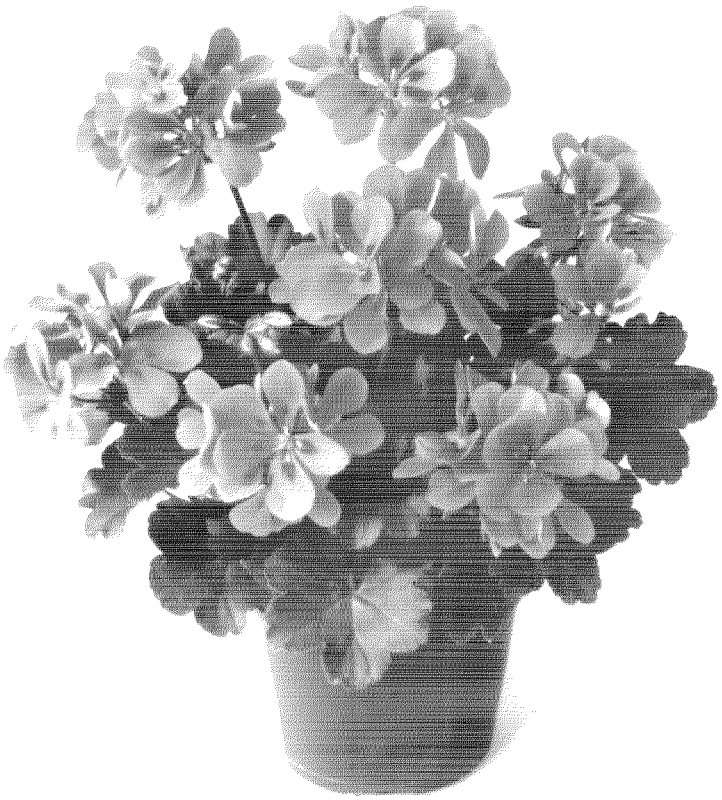

* * * * *